(12) United States Patent
Delaney, Jr. et al.

(10) Patent No.: US 10,667,896 B2
(45) Date of Patent: Jun. 2, 2020

(54) BIOABSORBABLE LEFT ATRIAL APPENDAGE CLOSURE WITH ENDOTHELIALIZATION PROMOTING SURFACE

(71) Applicant: CARDIAC PACEMAKERS, INC., St. Paul, MN (US)

(72) Inventors: Joseph Thomas Delaney, Jr., Minneapolis, MN (US); David Robert Wulfman, Minneapolis, MN (US); Sarah Melissa Gruba, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 413 days.

(21) Appl. No.: 15/349,156

(22) Filed: Nov. 11, 2016

(65) Prior Publication Data
US 2017/0135801 A1   May 18, 2017

Related U.S. Application Data

(60) Provisional application No. 62/254,969, filed on Nov. 13, 2015.

(51) Int. Cl.
*A61F 2/01* (2006.01)
*A61B 17/12* (2006.01)
*A61B 17/00* (2006.01)

(52) U.S. Cl.
CPC ............ *A61F 2/01* (2013.01); *A61B 17/1215* (2013.01); *A61B 17/12122* (2013.01);
(Continued)

(58) Field of Classification Search
CPC .......... A61B 17/12122; A61B 17/0057; A61B 17/12172; A61B 2017/00592; A61B 2017/00615; A61B 17/12022; A61B 2017/00243; A61B 2017/00575; A61B 2017/00597; A61B 17/12177;
(Continued)

(56) References Cited

U.S. PATENT DOCUMENTS

| 1,178,283 A | 6/1876 | French |
| 1,967,318 A | 7/1934 | Monahan |

(Continued)

FOREIGN PATENT DOCUMENTS

| DE | 102005053958 A1 | 5/2007 |
| DE | 102008015781 B1 | 9/2011 |

(Continued)

OTHER PUBLICATIONS

International search report for PCT/US2016/061543. 6 pages, dated May 18, 2017. (Year: 2017).*
"Filter". definition by Oxford Dicitonary <https://www.lexico.com/en/definition/filter> accessed on Aug. 15, 2019 (Year: 2019).*
"Absorb" definition by Merriam-Webster Dictionary <https://www.merriam-webster.com/dictionary/absorb> accessed on Aug. 15, 2019 Year: 2019).*

(Continued)

*Primary Examiner* — Katherine M Shi
(74) *Attorney, Agent, or Firm* — Seager, Tufte & Wickhem LLP (57) ABSTRACT

The disclosure pertains to percutaneously deliverable bioabsorbable closure devices for an ostium of a left atrial appendage which devices promote endothelialization across the ostium and then are bioabsorbed to leave little or no foreign residue, methods of manufacturing such bioabsorbable closure devices, and the use thereof.

9 Claims, 7 Drawing Sheets

(52) U.S. Cl.
CPC ............... *A61B 17/12145* (2013.01); *A61B 2017/00004* (2013.01); *A61B 2017/00526* (2013.01); *A61F 2002/011* (2013.01); *A61F 2002/016* (2013.01); *A61F 2210/0004* (2013.01); *A61F 2230/0093* (2013.01); *A61F 2240/001* (2013.01)

(58) Field of Classification Search
CPC . A61B 2017/00579; A61B 2017/00004; A61F 2/01; A61F 2002/018; A61F 2210/0004; A61F 2230/0093
USPC .................................................. 606/200, 213
See application file for complete search history.

(56) References Cited

U.S. PATENT DOCUMENTS

| | | |
|---|---|---|
| 3,844,302 A | 10/1974 | Klein |
| 3,874,388 A | 4/1975 | King et al. |
| 4,007,743 A | 2/1977 | Blake |
| 4,341,218 A | 7/1982 | Ü |
| 4,585,000 A | 4/1986 | Hershenson |
| 4,603,693 A | 8/1986 | Conta et al. |
| 4,665,906 A | 5/1987 | Jervis |
| 4,710,192 A | 12/1987 | Liotta et al. |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,078,736 A | 1/1992 | Behl |
| 5,108,420 A | 4/1992 | Marks |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,256,146 A | 10/1993 | Ensminger et al. |
| 5,258,042 A | 11/1993 | Mehta |
| 5,284,488 A | 2/1994 | Sideris |
| 5,306,234 A | 4/1994 | Johnson |
| 5,334,217 A | 8/1994 | Das |
| 5,350,399 A | 9/1994 | Erlebacher et al. |
| 5,353,784 A | 10/1994 | Nady-Mohamed |
| 5,370,657 A | 12/1994 | Irie |
| 5,375,612 A | 12/1994 | Cottenceau et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,509,899 A | 4/1996 | Fan et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,292 A | 7/1997 | Hart |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,702,421 A | 12/1997 | Schneidt |
| 5,709,224 A | 1/1998 | Behl et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,810,874 A | 9/1998 | Lefebvre |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,846,260 A | 12/1998 | Maahs |
| 5,846,261 A | 12/1998 | Kotula et al. |
| 5,849,005 A | 12/1998 | Garrison et al. |
| 5,851,232 A | 12/1998 | Lois |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,882,340 A | 3/1999 | Yoon |
| 5,885,258 A | 3/1999 | Sachdeva et al. |
| 5,895,399 A | 4/1999 | Barbut et al. |
| 5,902,289 A | 5/1999 | Swartz et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,931,818 A | 8/1999 | Werp et al. |
| 5,935,147 A | 8/1999 | Kensey et al. |
| 5,935,148 A | 8/1999 | Villar et al. |
| 5,941,249 A | 8/1999 | Maynard et al. |
| 5,944,738 A | 8/1999 | Amplatz et al. |
| 5,947,997 A | 9/1999 | Pavcnik et al. |
| 5,951,589 A | 9/1999 | Epstein et al. |
| 5,954,694 A | 9/1999 | Sunseri |
| 5,957,940 A | 9/1999 | Tanner et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,068,621 A | 5/2000 | Balceta et al. |
| 6,074,357 A | 6/2000 | Kaganov et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,132,438 A | 10/2000 | Fleischman et al. |
| 6,136,016 A | 10/2000 | Barbut et al. |
| 6,139,527 A | 10/2000 | Laufer et al. |

(56) References Cited

U.S. PATENT DOCUMENTS

| | | | |
|---|---|---|---|
| 6,152,144 A | 11/2000 | Lesh et al. |
| 6,161,543 A | 12/2000 | Cox et al. |
| 6,193,739 B1 | 2/2001 | Chevillon et al. |
| 6,203,531 B1 | 3/2001 | Ockuly et al. |
| 6,231,561 B1 | 5/2001 | Frazier et al. |
| 6,231,589 B1 | 5/2001 | Wessman et al. |
| 6,290,674 B1 | 9/2001 | Roue et al. |
| 6,328,727 B1 | 12/2001 | Frazier et al. |
| 6,328,755 B1 | 12/2001 | Marshall |
| 6,419,669 B1 | 7/2002 | Frazier et al. |
| 6,436,088 B2 | 8/2002 | Frazier et al. |
| 6,458,100 B2 | 10/2002 | Roue et al. |
| 6,533,782 B2 | 3/2003 | Howell et al. |
| 6,537,300 B2 | 3/2003 | Girton |
| 6,551,303 B1 | 4/2003 | Van Tassel et al. |
| 6,561,969 B2 | 5/2003 | Frazier et al. |
| 6,589,214 B2 | 7/2003 | McGuckin et al. |
| 6,595,989 B1 | 7/2003 | Schaer |
| 6,641,557 B1 | 11/2003 | Frazier et al. |
| 6,641,564 B1 | 11/2003 | Kraus |
| 6,650,923 B1 | 11/2003 | Lesh et al. |
| 6,652,555 B1 | 11/2003 | Van tassel et al. |
| 6,652,556 B1 | 11/2003 | Van tassel et al. |
| 6,673,053 B2 | 1/2004 | Wang et al. |
| 6,689,150 B1 | 2/2004 | Van tassel et al. |
| 6,702,825 B2 | 3/2004 | Frazier et al. |
| 6,712,804 B2 | 3/2004 | Roue et al. |
| 6,730,108 B2 | 5/2004 | Van Tassel et al. |
| 6,746,472 B2 | 6/2004 | Frazier et al. |
| 6,755,812 B2 | 6/2004 | Peterson et al. |
| 6,949,113 B2 | 9/2005 | Van Tassel et al. |
| 6,994,092 B2 | 2/2006 | Van Der Burg et al. |
| 7,011,671 B2 | 3/2006 | Welch |
| 7,025,756 B2 | 4/2006 | Frazier et al. |
| 7,044,134 B2 | 5/2006 | Khairkhahan et al. |
| 7,115,110 B2 | 10/2006 | Frazier et al. |
| 7,128,073 B1 | 10/2006 | Van Der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,338,514 B2 | 3/2008 | Wahr et al. |
| 7,427,279 B2 | 9/2008 | Frazier et al. |
| 7,544,381 B2 | 6/2009 | Kangas |
| 7,549,983 B2 | 6/2009 | Roue et al. |
| 7,566,336 B2 | 7/2009 | Corcoran et al. |
| 7,597,704 B2 | 10/2009 | Frazier et al. |
| 7,674,256 B2 | 3/2010 | Marrouche et al. |
| 7,713,282 B2 | 5/2010 | Frazier et al. |
| 7,722,641 B2 | 5/2010 | Van Der Burg et al. |
| 7,727,189 B2 | 6/2010 | Van tassel et al. |
| 7,735,493 B2 | 6/2010 | Van Der Burg et al. |
| 7,780,683 B2 | 8/2010 | Roue et al. |
| 7,914,809 B2 | 3/2011 | Atanasoska et al. |
| 7,972,359 B2 | 7/2011 | Kreidler |
| 8,034,061 B2 | 10/2011 | Amplatz et al. |
| 8,043,305 B2 | 10/2011 | Frazier et al. |
| 8,043,329 B2 | 10/2011 | Khairkhahan et al. |
| 8,048,060 B2 | 11/2011 | Griffin et al. |
| 8,052,715 B2 | 11/2011 | Quinn et al. |
| 8,080,032 B2 | 12/2011 | Van Der Burg et al. |
| 8,197,496 B2 | 6/2012 | Roue et al. |
| 8,197,527 B2 | 6/2012 | Borillo et al. |
| 8,221,384 B2 | 7/2012 | Frazier et al. |
| 8,221,445 B2 | 7/2012 | Van Tassel et al. |
| 8,287,563 B2 | 10/2012 | Khairkhahan et al. |
| 8,313,505 B2 | 11/2012 | Amplatz et al. |
| 8,323,309 B2 | 12/2012 | Khairkhahan et al. |
| 8,398,670 B2 | 3/2013 | Amplatz et al. |
| 8,454,633 B2 | 6/2013 | Amplatz et al. |
| 8,523,897 B2 | 9/2013 | Van Der Burg et al. |
| 8,535,343 B2 | 9/2013 | Van Der Burg et al. |
| 2001/0039434 A1 | 11/2001 | Frazier et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0111647 A1 | 8/2002 | Khairkhahan |
| 2003/0023266 A1 | 1/2003 | Borillo et al. |
| 2003/0057156 A1 | 3/2003 | Peterson et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0212432 A1 | 11/2003 | Khairkhahan et al. |
| 2003/0220667 A1 | 11/2003 | Van Der Burg et al. |
| 2004/0034366 A1 | 2/2004 | Van Der Burg et al. |
| 2004/0044361 A1 | 3/2004 | Frazier et al. |
| 2004/0098031 A1 | 5/2004 | Van Der Burg et al. |
| 2004/0186486 A1 | 9/2004 | Roue et al. |
| 2004/0215169 A1 | 10/2004 | Li |
| 2004/0215230 A1 | 10/2004 | Frazier et al. |
| 2004/0220595 A1 | 11/2004 | Frazier et al. |
| 2004/0230222 A1 | 11/2004 | Van Der Burg et al. |
| 2005/0004652 A1 | 1/2005 | Van Der Burg et al. |
| 2005/0038470 A1 | 2/2005 | Van Der Burg et al. |
| 2005/0070952 A1 | 3/2005 | Devellian |
| 2005/0125032 A1 | 6/2005 | Whisenant et al. |
| 2005/0149115 A1 | 7/2005 | Roue et al. |
| 2005/0177182 A1 | 8/2005 | Van Der Burg et al. |
| 2005/0192627 A1 | 9/2005 | Whisenant et al. |
| 2005/0203568 A1 | 9/2005 | Burg et al. |
| 2005/0234543 A1 | 10/2005 | Glaser et al. |
| 2005/0288706 A1* | 12/2005 | Widomski ......... A61B 17/0057 606/213 |
| 2006/0184234 A1 | 8/2006 | Frazier et al. |
| 2006/0206148 A1 | 9/2006 | Khairkhahan et al. |
| 2007/0066993 A1 | 3/2007 | Kreidler |
| 2007/0066994 A1 | 3/2007 | Blaeser et al. |
| 2007/0080188 A1 | 4/2007 | Spence et al. |
| 2007/0083227 A1 | 4/2007 | Van Der Burg et al. |
| 2007/0112380 A1 | 5/2007 | Figulla et al. |
| 2007/0129753 A1 | 6/2007 | Quinn et al. |
| 2007/0135826 A1 | 6/2007 | Zaver et al. |
| 2007/0162048 A1 | 7/2007 | Quinn et al. |
| 2008/0071307 A1* | 3/2008 | DeBruyne ................ A61F 2/07 606/200 |
| 2008/0071350 A1 | 3/2008 | Stinson |
| 2008/0071358 A1 | 3/2008 | Weber et al. |
| 2009/0028785 A1 | 1/2009 | Clarke |
| 2009/0098176 A1 | 4/2009 | Helmus et al. |
| 2010/0069838 A1 | 3/2010 | Weber et al. |
| 2010/0087783 A1 | 4/2010 | Weber et al. |
| 2011/0054515 A1 | 3/2011 | Bridgeman et al. |
| 2011/0218566 A1 | 9/2011 | Van Der Burg et al. |
| 2012/0029541 A1 | 2/2012 | Frazier et al. |
| 2012/0029553 A1 | 2/2012 | Quinn et al. |
| 2012/0035643 A1 | 2/2012 | Khairkhahan et al. |
| 2012/0065662 A1 | 3/2012 | Van Der Burg et al. |
| 2012/0065667 A1* | 3/2012 | Javois ............. A61B 17/12122 606/213 |
| 2012/0095396 A1 | 4/2012 | Radhakrishnan et al. |
| 2012/0232585 A1 | 9/2012 | Roue et al. |
| 2012/0239077 A1 | 9/2012 | Zaver et al. |
| 2012/0239083 A1 | 9/2012 | Kreidler |
| 2013/0012982 A1 | 1/2013 | Khairkhahan et al. |
| 2013/0018413 A1* | 1/2013 | Oral ..................... A61B 5/0031 606/213 |
| 2013/0110154 A1 | 5/2013 | Van Der Burg et al. |
| 2013/0138138 A1* | 5/2013 | Clark ............... A61B 17/12022 606/200 |
| 2014/0074151 A1 | 3/2014 | Tischler et al. |

FOREIGN PATENT DOCUMENTS

| | | | |
|---|---|---|---|
| EP | 1223890 B1 | 4/2004 |
| EP | 1227770 B1 | 9/2004 |
| EP | 1616530 B1 | 10/2008 |
| EP | 1659988 B1 | 2/2010 |
| EP | 1620020 B1 | 9/2010 |
| EP | 1135068 B1 | 6/2011 |
| EP | 1441649 B1 | 8/2011 |
| JP | 2014533970 A | 12/2014 |
| JP | 2015509752 A | 4/2015 |

(56) References Cited

FOREIGN PATENT DOCUMENTS

| | | |
|---|---|---|
| WO | 913712 A1 | 7/1993 |
| WO | 9721402 A1 | 6/1997 |
| WO | 9726939 A1 | 7/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9907289 A1 | 2/1999 |
| WO | 9908607 A1 | 2/1999 |
| WO | 9912478 A1 | 3/1999 |
| WO | 9930640 A1 | 6/1999 |
| WO | 9959479 A1 | 11/1999 |
| WO | 0001308 A1 | 1/2000 |
| WO | 0027292 A1 | 5/2000 |
| WO | 0053120 A1 | 9/2000 |
| WO | 0121247 A1 | 3/2001 |
| WO | 0126726 A1 | 4/2001 |
| WO | 0130266 A1 | 5/2001 |
| WO | 0130267 A1 | 5/2001 |
| WO | 0130268 A1 | 5/2001 |
| WO | 2002071977 A2 | 9/2002 |
| WO | 2003007825 A1 | 1/2003 |
| WO | 2003063732 A2 | 8/2003 |
| WO | 2004096060 A2 | 11/2004 |
| WO | 2007054116 A1 | 5/2007 |
| WO | 2007140797 A1 | 12/2007 |
| WO | 2008125689 A1 | 10/2008 |
| WO | 2009091425 A1 | 7/2009 |
| WO | 2011147783 A1 | 12/2011 |
| WO | 2014210263 A1 | 12/2014 |

OTHER PUBLICATIONS

Cragg et al., "A New Percutaneous Vena Cava Filter," ALJ, 141: 601-604, Sep. 1983.
Cragg et al., "Nonsurgical Placement of Arterial Endoprothesis: A New Technique Using Nitinol Wire," Radiology, 147(1): 261-263, Apr. 1983.
Lock et al., "Transcatheter Closure of Atrial Septal Defects," Circulation, 79(5): 1091-1099, May 1989.
Lock et al., "Transcatheter Umbrella Closure of Congenital Heart Defects," Circulation, 75(3): 593-599, 1987.
Rashkind et al., "Nonsurgical Closure of Patent Ductus Arteriosus: Clinical Application of the Rashking PDA Occluder System," Circulation, 75(3): 583-592, 1987.
Ruttenberg, "Nonsurgical Therapy of Cardiac Disorders," Pediatric Consult, 5(2), 1986.
Sugita et al., "Nonsurgical Implantation of a Vascular Ring Prothesis Using Thermal Shape Memory Ti/Ni Alloy (Nitnol Wire)," Trans. Am. Soc. Artif. Intern. Organs, XXXII: 30-34, 1986.
Wessel et al., "Outpatient Closure of the Patent Ductus Arteriosus," Circulation, 77(5): 1068-1071, 1988.
Khattab et al., "Transcatheter Devices for Left Atrial Appendage Occlusion," Cardiovascular Medicine, 13(4): 130-134, 2010.
Amplatzer Vascular Plug Family, http://web.archive.org/web/20100514232852/http://international.amplatzer.com/InternationalProducts/VascularPlugFamily/tabid/528/Default.aspx, accessed Oct. 9, 2013, and said, by the Wayback Machine, to have been archived on May 14, 2010.
Amplatzer Cardiac Plug, http://web.archive.org/web/20090809150223/http:/international.amplatzer.com/international_products/CardiacPlug/tabid/815/default.aspx, accessed Oct. 9, 2013, and said, by the Wayback Machine, to have been archived on Aug. 9, 2009.

\* cited by examiner

BIOABSORBABLE LEFT ATRIAL APPENDAGE CLOSURE WITH ENDOTHELIALIZATION PROMOTING SURFACE

RELATED APPLICATIONS

This application claims the benefit of U.S. Provisional Application No. 62/254,969, filed Nov. 13, 2015.

BACKGROUND

There are a number of heart diseases (e.g. coronary artery disease, mitral valve disease) that have various adverse effects on the heart. An adverse effect of certain cardiac diseases, such as mitral valve disease, is atrial (or auricular) fibrillation. Atrial fibrillation may result in pooling of blood in the left atrial appendage. Blood pooling may also be spontaneous. When blood pools in the atrial appendage, blood clots can form and accumulate therein, build upon themselves, and propagate out from the atrial appendage into the atrium. These blood clots can then enter the systemic or pulmonary circulations and cause serious problems if they migrate from the atrial appendage and become free in the blood stream and embolize distally into the arterial system. Similar problems also occur when a blood clot extending from an atrial appendage into an atrium breaks off and enters the blood supply. Since blood from the left atrium and ventricle supply the heart and brain, blood clots from the atrial appendages can obstruct blood flow therein causing heart attacks, strokes or other organ ischemia. It is therefore necessary to find a means of preventing blood clots from forming in the atrial appendages and to prevent these blood clots, once formed, from leaving the atrial appendages to the heart lungs, brain or other circulations of the patient which can cause heart attacks or strokes or other organ ischemia.

U.S. Pat. No. 5,865,791 relates to the reduction of regions of blood stasis and ultimately thrombus formation in such regions, particularly in the atrial appendages of patients with atrial fibrillation. More specifically, the invention relates to procedures and devices for affixing the atrial appendages in an orientation that prevents subsequent formation of thrombus. The invention removes the appendage from the atrium by pulling on it and putting a loop around it to form a sack of the atrial appendage and then cut off from the rest of the heart.

U.S. Pat. No. 5,306,234 relates to a method for surgically closing the passage between the atrium and the atrial appendage or severing the atrial appendage.

U.S. Pat. Nos. 6,551,303 and 6,689,150 disclose barrier devices and filter devices respectively which may be deployed at the ostium of a left atrial appendage to block thrombus generated within the left atrial appendage from entering the left atrium and general circulation.

While current treatment methods are effective for minimizing migration of thrombus from the left atrial appendage into the general circulation, a need still exists for a percutaneous treatment option which does not result in the long term introduction of foreign matter which may provoke an inflammatory response.

SUMMARY

In some aspects, the invention relates to a left atrial appendage closure device comprising a plurality of centrally joined bioabsorbable struts forming an umbrella-like support structure which is concave when viewed from a distal end of the plurality of centrally joined bioabsorbable struts, wherein the umbrella-like support structure has a first radially compact configuration and a second expanded configuration in which second expanded configuration the umbrella-like support structure has a proximal circumferential dimension sized and adapted to span the ostium of a left atrial appendage and a distal extent sized and adapted to be contained within the left atrial appendage; a bioabsobable porous membrane which forms a porous cap coextensive with centrally joined portions of the bioabsorbable struts and which extends distally along at least a portion of the umbrella-like support structure sized and adapted to be contained within the left atrial appendage, wherein the porous membrane is bioabsorbable, the pores of the porous membrane are sized and adapted to retain thrombi within the left atrial appendage when the left atrial appendage closure device is deployed within the left atrial appendage, and the porous membrane includes a tissue growth promoting component. In some aspects, at least some of the bioabsorbable struts of the umbrella-like support structure may be joined near their distal ends to form a closed support structure cage.

In addition or alternatively, the invention relates to a left atrial appendage closure device wherein the bioabsorbable porous membrane is selected from the group consisting of a textile, a nonwoven, a braid, a laser cut sheet, an etched sheet, and a 3D printed article.

In some aspects, the bioabsorbable polymer of the plurality of centrally joined bioabsorbable struts and the polymer of the bioabsorbable porous membrane of the left atrial appendage closure device are selected from the group consisting of polyglycolic acid, polylactic acid, polycaprolactone, polyvalerolactone, poly(1,4-dioxane-2,3-dione), poly(1,3-dioxane-2-one), poly(p-dioxanone), poly(1,5-dioxepan-2-one), poly(β-R,S-malic acid), poly(α-malic acid), polyhydroxyalkanoates, and mixtures or copolymers thereof.

In some aspects of the invention, the polymer of the plurality of bioabsorbable struts is the same as the polymer of the bioabsorbable porous membrane.

In some aspects of the invention, the polymer of the plurality of centrally joined bioabsorbable struts is different from the polymer of the bioabsorbable porous membrane.

In certain aspects of the invention, the porous membrane includes a tissue growth promoting component selected from the group consisting of fibronectin, vascular endothelial growth factor, and fibroblast growth factor.

In some aspects of the invention the tissue growth promoting component of the left atrial appendage closure device is a layer on the porous membrane.

In certain aspects of the invention the tissue growth promoting component of the left atrial appendage closure device is dispersed within the bioabsorbable porous membrane.

In addition, the thicknesses of the struts of the plurality of centrally joined bioabsorbable struts and of the bioabsorbable porous membrane of the left atrial appendage device of the invention are selected to provide a controlled bioabsorption profile which minimizes release of particulate material.

In some aspects of the invention, the left atrial appendage closure device further comprises a hub which is attached to the centrally joined plurality of bioabsorbable struts and adapted to be releaseably attached to a distal end of a delivery shaft.

In addition or alternatively, the invention includes a method of manufacturing a left atrial appendage closure device comprising the steps of creating a plurality of centrally joined bioabsorbable struts forming an umbrella-like support structure and creating a porous bioabsorbable membrane which forms a porous cap coextensive with centrally joined portions of the bioabsorbable struts and extending distally along at least a portion of the umbrella-like support structure, wherein the porous membrane is fixedly attached to the plurality of centrally joined bioabsorbable struts forming an umbrella-like support structure and wherein the porous membrane includes a tissue growth promoting component. In some aspects of the method of manufacturing a left atrial appendage closure device, at least some of the distal ends of the bioabsorbable struts forming an umbrella-like support structure may be joined to form a closed support structure cage.

In certain aspects of the method of manufacturing a left atrial appendage closure device of the invention, the step of creating the plurality of centrally joined bioabsorbable struts forming an umbrella-like support structure includes one or more of welding, molding, vacuum forming, removing material from a solid workpiece, and 3D printing.

In some aspects of the method of manufacturing a left atrial appendage closure device, the step of creating the porous bioabsorbable membrane which forms a porous cap coextensive with centrally joined portions of the bioabsorbable struts and which extends distally along at least a portion of the umbrella-like support structure includes one or more of weaving, braiding, electrospraying, electrospinning, molding, vacuum forming, laser cutting, etching, and 3D printing.

In addition or alternatively, in the method of manufacturing a left atrial appendage closure device of the invention, the step of creating a plurality of centrally joined bioabsorbable struts forming an umbrella-like support structure and the step of creating a porous bioabsorbable membrane which forms a porous cap coextensive with centrally joined portions of the bioabsorbable struts and which extends distally along at least a portion of the umbrella-like support structure are carried out simultaneously to create a unitary left atrial appendage closure device. In some aspects, at least some of the bioabsorbable struts of the umbrella-like support structure may be joined near their distal ends to form a closed support structure cage.

In addition or alternatively the method of manufacturing a left atrial appendage closure device further comprises attaching a hub to the centrally joined bioabsorbable struts, said hub being adapted to be releaseably attached to a distal end of a delivery shaft.

In some aspects of the invention, left atrial appendage closure device comprises a plurality of bioabsorbable struts having a proximal end and a distal end which are joined at their proximal portions to form an umbrella-like support structure which is concave when viewed from a distal end of the plurality of proximally joined bioabsorbable struts, wherein the umbrella-like support structure has a first compact delivery configuration and a second expanded deployed configuration in which the umbrella-like support structure has a proximal circumferential dimension sized and adapted to span and engage the ostium of a left atrial appendage and a longitudinal extent sized and adapted to be contained within the left atrial appendage; a bioabsorbable porous cap coextensive with the joined proximal portions of the bioabsorbable struts and which extends distally therefrom along at least a portion of the umbrella-like support structure sized and adapted to be contained within the left atrial appendage, wherein the porous cap is bioabsorbable, the pores of the porous cap are sized and adapted to retain thrombi within the left atrial appendage when the left atrial appendage closure device is deployed within the left atrial appendage, and the porous cap includes a tissue growth promoting component. In some aspects, at least some of the bioabsorbable struts of the umbrella-like support structure may be joined near their distal ends to form a closed support structure cage.

In some aspects, the bioabsorbable porous cap of the left atrial appendage closure device of the invention is selected from the group consisting of a textile, a nonwoven, a braid, a laser cut sheet, an etched sheet, and a 3D printed article.

In addition, the bioabsorbable polymer of the plurality of proximally joined bioabsorbable struts and the polymer of the bioabsorbable porous cap of the left atrial appendage closure device of the invention are selected from the group consisting of polyglycolic acid, polylactic acid, polycaprolactone, polyvalerolactone, poly(1,4-dioxane-2,3-dione), poly(1,3-dioxane-2-one), poly(p-dioxanone), poly(1,5-diox-epan-2-one), poly(β-R,S-malic acid), poly(α-malic acid), polyhydroxyalkanoates, and mixtures or copolymers thereof.

In some aspects of the invention, the polymer of the plurality of bioabsorbable struts is the same as the polymer of the bioabsorbable porous cap.

In certain aspects of the invention, the plurality of proximally joined bioabsorbable struts and the bioabsorbable porous cap of the left atrial appendage closure device are integrally formed.

In some aspects of the invention, the polymer of the plurality of proximally joined bioabsorbable struts of left atrial appendage closure device of the invention is different from the polymer of the bioabsorbable porous cap.

In certain aspects of the invention, the tissue growth promoting component of the left atrial appendage closure device is selected from the group consisting of fibronectin, vascular endothelial growth factor, and fibroblast growth factor.

In some aspects of the invention, tissue growth promoting component of the left atrial appendage device of the invention is a layer on the bioabsorbable porous cap.

In addition or in the alternative, the tissue growth promoting component of the left atrial appendage device of the invention is dispersed within the bioabsorbable porous cap.

In addition or in the alternative, the tissue growth promoting component of the left atrial appendage device of the invention is absorbed within a surface layer of the bioabsorbable porous cap.

In some aspects of the invention, the thicknesses of the plurality of proximally joined bioabsorbable struts and the bioabsorbable porous cap of the left atrial appendage closure device are selected to provide a controlled bioabsorption profile which minimizes release of particulate material.

In addition or in the alternative, the left atrial appendage closure device further comprises a hub attached to the plurality of proximally joined bioabsorbable struts and adapted to be releaseably attached to a distal end of a delivery shaft.

In addition or in the alternative, the invention includes a method of manufacturing a left atrial appendage closure device comprising the steps of creating a plurality of bioabsorbable struts joined at their proximal portions to form a distally opening umbrella-like support structure and creating a porous bioabsorbable cap coextensive with proximally joined portions of the bioabsorbable struts and extending distally along at least a portion of the umbrella-like support structure, wherein the bioabsorbable porous cap is fixedly attached to the plurality of proximally joined bioabsorbable struts forming an umbrella-like support structure and wherein the bioabsorbable porous cap includes a tissue growth promoting component. In some aspects, at least some of the bioabsorbable struts of the umbrella-like support structure may be joined near their distal ends to form a closed support structure cage.

In certain aspects of the method of manufacturing a left atrial appendage closure device, the step of creating the plurality of bioabsorbable struts joined at their proximal portions to form a distally opening umbrella-like support structure includes one or more of welding, molding, vacuum forming, removing material from a solid workpiece, and 3D printing. In some aspects, at least some of the bioabsorbable struts of the umbrella-like support structure may be joined near their distal ends to form a closed support structure cage.

In some aspects of the method of manufacturing a left atrial appendage closure device of the invention, the step of creating the bioabsorbable porous cap which forms a porous cap coextensive with proximally joined portions of the bioabsorbable struts and which extends distally along at least a portion of the umbrella-like support structure includes one or more of weaving, braiding, electrospraying, electrospinning, molding, vacuum forming, laser cutting, etching, and 3D printing.

In the alternative or in addition, the method of manufacturing a left atrial appendage closure device of claim 28, wherein the steps of creating a plurality of bioabsorbable struts joined at their proximal portions to form a distally opening umbrella-like support structure and creating a porous bioabsorbable membrane which forms a porous cap coextensive with the plurality of bioabsorbable struts joined at their proximal portions to form a distally opening umbrella-like support structure which extends distally along at least a portion of the umbrella-like support structure are carried out simultaneously to create a unitary left atrial appendage closure device. In some aspects, at least some of the bioabsorbable struts of the umbrella-like support structure may be joined near their distal ends to form a closed support structure cage.

In some aspects of the method of manufacturing a left atrial appendage closure device of the invention, the bioabsorbable polymer of the plurality of bioabsorbable struts and of the bioabsorbable porous cap is selected from the group consisting of polyglycolic acid, polylactic acid, polycaprolactone, polyvalerolactone, poly(1,4-dioxane-2,3-dione), poly(1,3-dioxane-2-one), poly(p-dioxanone), poly(1,5-dioxepan-2-one), poly(β-R,S-malic acid), poly(α-malic acid), polyhydroxyalkanoates, and mixtures or copolymers thereof.

In certain aspects of the method of manufacturing a left atrial appendage closure device of the invention the tissue growth promoting component is selected from the group consisting of fibronectin, vascular endothelial growth factor, and fibroblast growth factor.

In addition or in the alternative, the method of manufacturing a left atrial appendage closure device of the invention further comprises a step of attaching a hub to the plurality of bioabsorbable struts joined at their proximal ends, said hub being adapted to be releaseably attached to a distal end of a delivery shaft.

In some aspects of the method of manufacturing a left atrial appendage closure device the invention, the hub is a bioabsorbable hub.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings exemplify aspects of the claimed invention.

Although some suitable dimensions, ranges and/or values pertaining to various components, features and/or specifications are disclosed, one of skill in the art, incited by the present disclosure, would understand desired dimensions, ranges and/or values may deviate from those expressly disclosed unless the context clearly indicates an intended limitation.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an aspect", "some aspects", "other aspects", etc., indicate that the aspect described may include a particular feature, structure, or characteristic, but not every aspect may necessarily include the particular feature, structure, or characteristic. Moreover, such phrases are not necessarily referring to the same aspect of the invention. Further, when a particular feature, structure, or characteristic is described in connection with an aspect, it would be within the knowledge of one skilled in the art to effect such feature, structure, or characteristic in connection with other embodiments whether or not explicitly described unless clearly stated to the contrary.

Figure 1A:
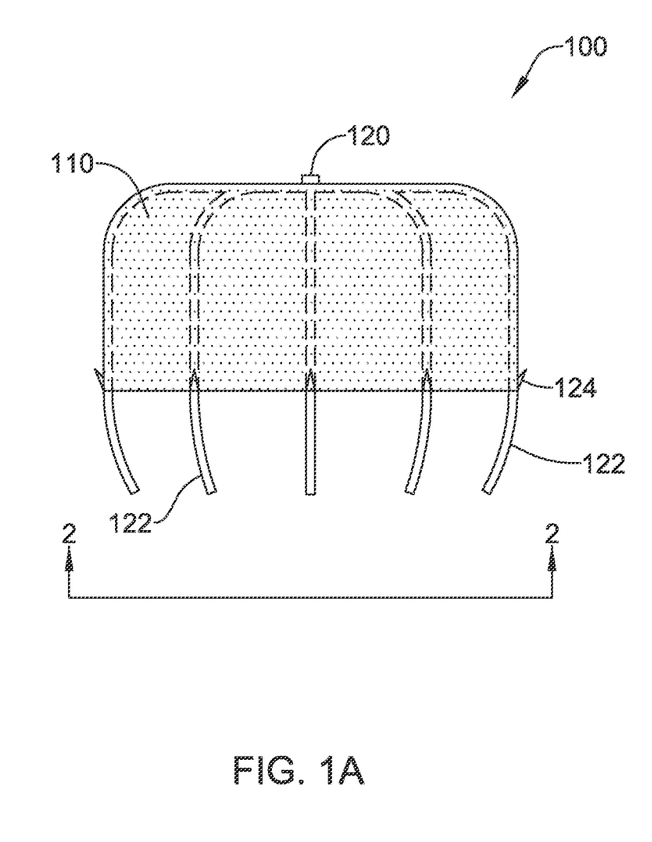
FIG. 1A presents a lateral view of a left atrial appendage closure device of the invention.
Figure 2:
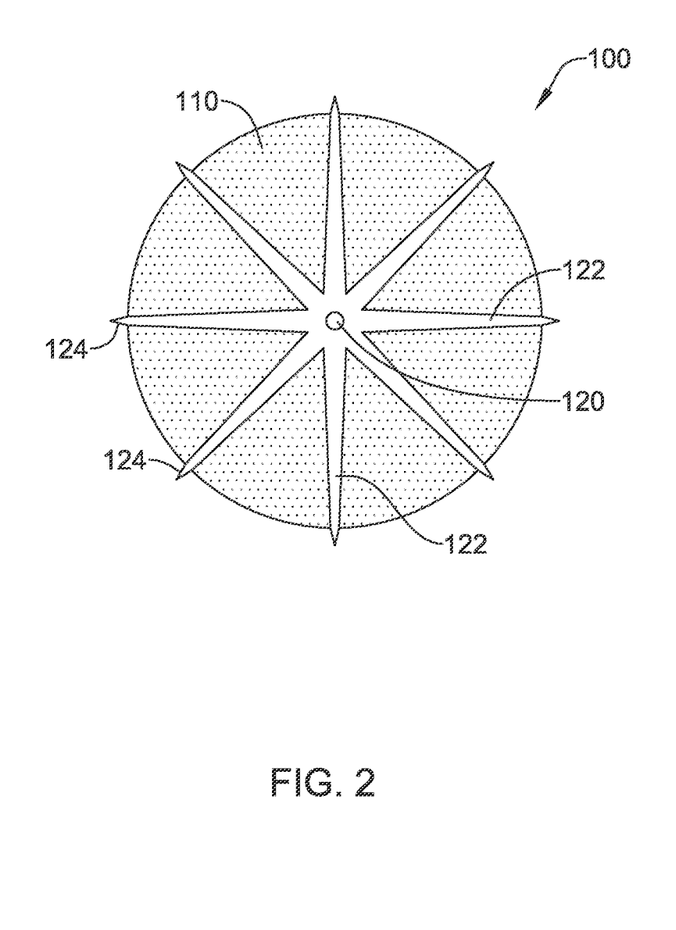
FIG. 2 presents an axial view of the left atrial appendage closure device of FIG. 1A as seen from the distal end thereof.

FIG. 1A shows a lateral view of an expanded self-expanding left atrial appendage closure device 100 and FIG. 2 shows a axial view of the same device as seen from the distal end, which device comprises a plurality of bioabsorbable struts 122, each having a proximal end and a distal end, which are joined at their proximal portions to form an umbrella-like support structure which is concave when viewed from a distal end of the plurality of proximally joined bioabsorbable struts; a porous cap 110 coextensive with the joined proximal portions of the bioabsorbable struts 122 and extending distally therefrom along at least a portion of the bioabsorbable struts 122. In some aspects, at least some of the bioabsorbable struts of the umbrella-like support structure may be joined near their distal ends to form a closed support structure cage.

Although the illustrated aspect of the invention has eight bioabsorbable struts 122, it will be appreciated that more or fewer bioabsorbable struts, for example, 4, 5, 6, 7, 9, 10, or 12 struts, may be employed if desired. Generally fewer struts may reduce the diameter of a collapsed configuration of a left atrial appendage closure device 100 to facilitate delivery, while the addition of more bioabsorbable struts 122 may tend to provide a smoother wall sealing contour by allowing individual bioabsorbable struts 122 flex to a greater or lesser extent to accommodate variations in the shape of an ostium. In some aspects of the invention, at least some of the bioabsorbable struts may be joined at their distal ends to form a closed cage support structure.

The proximal ends of the plurality of bioabsorbable struts 122 may assume a generally planar configuration adapted to span the ostium of a left atrial appendage before bending distally to provide a more cylindrical wall engaging portion. The joined proximal ends may form or include a hub 120 to be discussed in greater detail below. In some aspects of the invention, the hub 120 may be formed as a thickened region of the joined proximal ends of the plurality of bioabsorbable struts 122. Although shown in the figures as slightly protruding proximally from the porous cap 110 in the figures for clarity of illustration, it will be appreciated that the hub may be constructed to be flush with the porous cap 110 or even slightly recessed therefrom.

Bioabsorbable struts 122 may also include one or more optional barbs 124 to be discussed in greater detail later.

The invention contemplates a variety of cross-sectional shapes and cross-sectional areas distributed along the length of the struts which are selected to control the rate of bioabsorption in a manner which provides adequate support during endothelialization, provides rapid bioabsorption when support is no longer required, and which minimizes the release of portions of the biodegradable struts 122 and/or the porous cap 110 membrane which might otherwise constitute undesirable particulate matter debris within the circulatory system.

Figure 5:
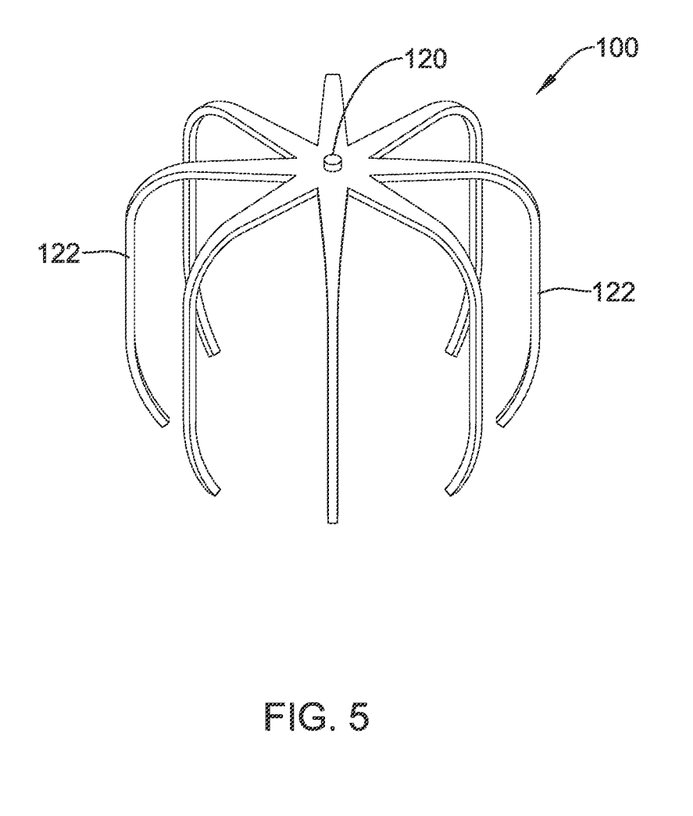
FIG. 5 illustrates a plurality of centrally joined struts of a left atrial appendage closure device of the invention.

The bioabsorbable struts 122 and the resulting umbrella-like structure may be formed by any of the methods employed in the art to construct similar structures and may include injection molding, blow molding, machining, 3D printing and assembly from individual components. In certain aspects of the invention, the bioabsorbable struts 122 or 122' and hub 120 may be formed as a separate membrane supporting structure as shown in FIG. 5. In some aspects of the invention, the bioabsorbable struts 122 may be formed from one or more of polyglycolic acid, polylactic acid, polycaprolactone, polyvalerolactone, poly(1,4-dioxane-2,3-dione), poly(1,3-dioxane-2-one), poly(p-dioxanone), poly (1,5-dioxepan-2-one), poly(β-R,S-malic acid), poly(α-malic acid), polyhydroxyalkanoates, mixtures or copolymers thereof, and the like. In an exemplary aspect, the bioabsorbable struts 122 may be formed from poly-4-hydroxybutyrate and copolymers thereof.

Figure 1B:
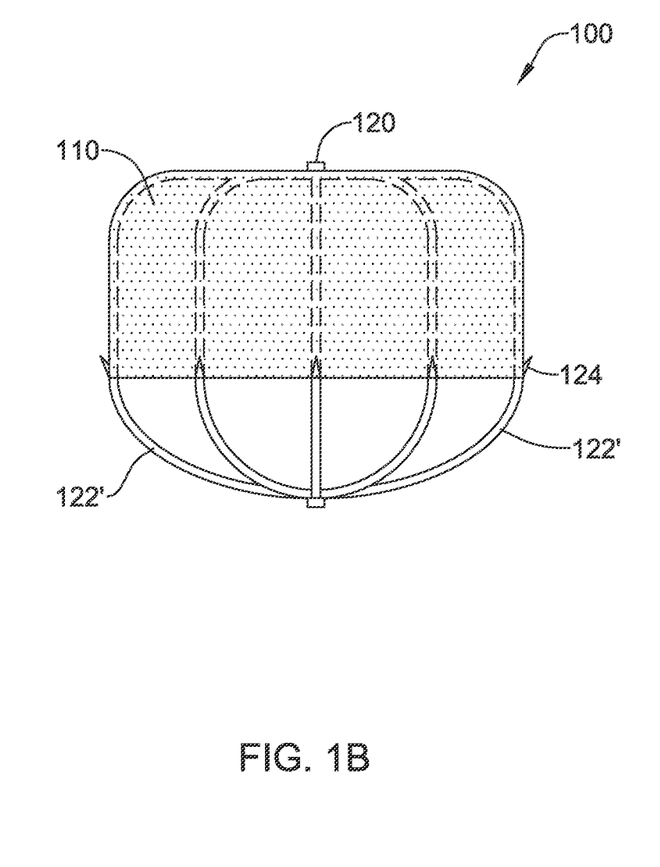
FIG. 1B illustrates an alternate arrangement of the plurality of centrally joined struts of a left atrial appendage closure device of the invention.

The porous cap 110 of FIGS. 1 and 2 may be viewed as providing a generally planar central region which is adapted to span an ostium of a left atrial appendage as well as transitioning to provide a generally cylindrical skirt which is adapted to lie along a lumen wall defined by a left atrial appendage and to improve the lateral sealing ability of the porous cap 110 within the left atrial appendage once the device is deployed.

The porous cap 110 is formed from a bioabsorbable membranous material which may comprise one or more of polyglycolic acid, polylactic acid, polycaprolactone, polyvalerolactone, poly(1,4-dioxane-2,3-dione), poly(1,3-dioxane-2-one), poly(p-dioxanone), poly(1,5-dioxepan-2-one), poly(β-R,S-malic acid), poly(α-malic acid), polyhydroxyalkanoates, mixtures or copolymers thereof, and the like. In an exemplary aspect, the porous cap 110 membrane may be formed from poly-4-hydroxybutyrate and copolymers thereof.

The porous cap 110 membrane may be a textile, a nonwoven, a braid, a laser cut sheet, an etched sheet or a 3D printed article. In some aspects, the porous cap 110 membrane may be formed by one or more of weaving, braiding, electrospraying, electrospinning, molding, vacuum forming, laser cutting, etching, and 3D printing. While the pores of the porous cap 110 membrane have been depicted as through pores for ease of illustration in some of the figures, it will be appreciated that for the purpose of promoting tissue ingrowth of endothelial tissue, some or all of the porosity may be disposed at or near the surface of the porous cap 110 membrane. Although illustrated in the figures as disposed over the bioabsorbable struts 122, it will be appreciated that the porous cap 110 membrane may in the alternative be disposed within a support structure provided by bioabsorbable struts 122.

It also will be appreciated that it may be convenient to form the plurality of centrally joined bioabsorbable struts 122 and the porous cap 110 membrane simultaneously as an integrally formed object. In those aspects, it may be desirable to include one or more additional components of the left atrial appendage closure device 100 such as hub 120, barbs 124 or their equivalents, a tissue growth promoter 112, 114, and the like in the same forming operation. In addition, in such aspects the portions of the bioabsorbable struts 122 which are coextensive with the porous cap 110 membrane may be present as thickened portions of the porous cap 110 membrane rather than as distinctly separate features.

The hub 120, barbs 124 or their equivalents, a tissue growth promoter 112, 114, and the like may also be introduced at different stages of the manufacturing operation if desired. Similarly, it may be desirable or convenient to use the same or different bioabsorbable polymers for various components of the left atrial appendage closure device as well as the same or different manufacturing processes for the fabrication of individual components to be assembled in separate steps of a manufacturing method.

In the aspect of the invention illustrated in FIGS. 1 and 2, each bioabsorbable strut 122 includes an optional barb 124 which is sized and adapted to engage adjacent tissue to minimize migration of a deployed device. Although one barb 124 is shown on each bioabsorbable strut 122, one of ordinary skill in the art would appreciate that this arrangement is only illustrative of an aspect of the invention. In other aspects, a strut or struts may have 0, 2, 3, or more barbs per bioabsorbable strut 122 and not every bioabsorbable strut 122 needs to have the same number of barbs 124 as its immediate neighbors. The simple barb 124 of FIGS. 1 and 2 is intended to be representative of other structures known in the art to inhibit migration of an implanted device. For example, the simple barb 124 of FIGS. 1 and 2 may be replaced by a two-tipped barb having one tip disposed generally in a proximal direction along the associated bioabsorbable strut while a second tip is disposed generally in a distal direction along the associated bioabsorbable strut 122. Similarly, the barb 124 may be replaced with a roughened segment of exposed bioabsorbable strut 122 such that each protrusion from the roughened segment of exposed bioabsorbable strut 122 may be viewed as a tip of a barb 124. Some barbs 124 may be integrally formed with the associated strut while other barbs 124 may be formed separately and attached to the bioabsorbable strut 122. It will be appreciated that although the exemplary barbs 124 are illustrated as located at the distal margin of the porous cap 110 membrane, barbs 124 or their equivalents may be distributed at other locations along the associated bioabsorbable strut 122 and may extend outward from the surface of the porous cap 110 membrane as well as outward from more distal portions of the bioabsorbable struts 122. As discussed above, barbs 124 or their equivalents, if present, also may be formed from the previously identified bioabsorbable polymer(s) using the known manufacturing processes.

Figure 6A:
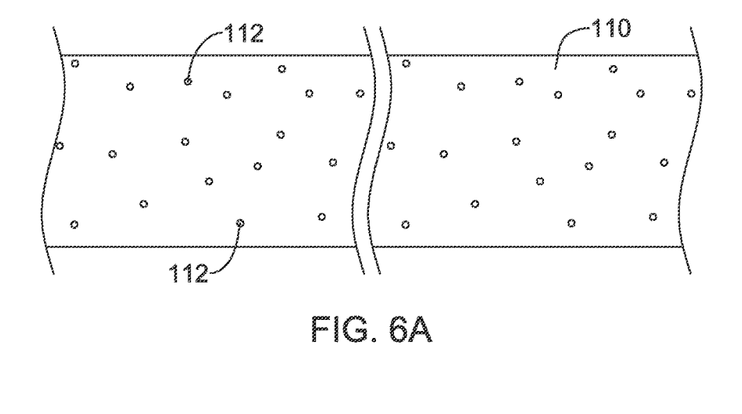
FIGS. 6A and 6B provide schematic cross-sectional views of portions of porous cap membranes of the invention which include a tissue growth promoting component.
Figure 6B:
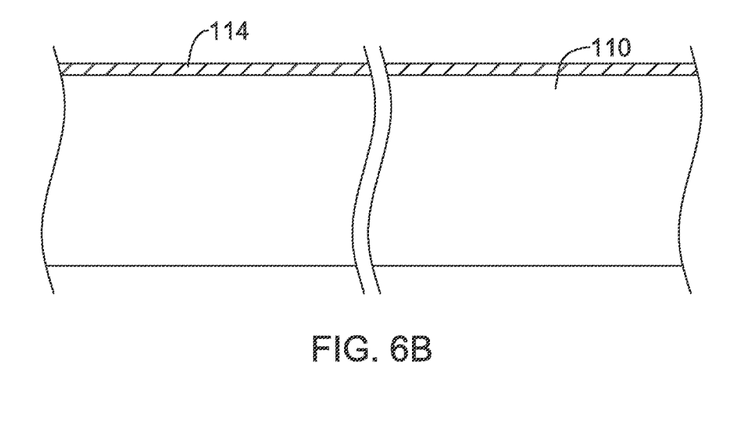

In the interest of promoting tissue growth into and across the portion of the porous cap 110 membrane located at the ostium of the left atrial appendage to permanently seal the ostium prior to the full bioabsorption of the left atrial appendage closure device 100, the devices include a tissue growth promoting component 112, 114 which may be dispersed throughout the porous cap 110 membrane as shown in FIG. 6A, preferentially absorbed near one or both surfaces of the porous cap 110 membrane, and/or applied as a coating to one or both surfaces of the porous cap 110 membrane as shown if FIG. 6B. If desired or convenient, the tissue growth promoting component 112, 114 may also be present within or applied to other components of the left atrial appendage closure device 100 such as the bioabsorbable struts 122 and barbs 124 or their equivalents.

In a further aspect related to the manufacturing of a left atrial appendage closure device 100, a support structure shown in FIG. 5 provided by bioabsorbable struts 122 comprising poly-4-hydroxybutyrate may be formed separately by, for example, injection molding and then positioned about a mandrel. In an alternate aspect of the manufacturing method, a support structure shown in FIG. 1B, in which at least some of the bioabsorbable struts 122' may also be joined at their distal end. In a separate step, a porous cap 110 membrane may be formed over a portion of the bioabsorbable struts 122 and the mandrel by electrospinning filaments of poly-4-hydroxybutyrate. In some aspects, the bioabsorbable struts 122 may be removed from the mandrel and a porous cap 110 membrane may be formed over a portion of the bioabsorbable struts 122 and the mandrel by electrospinning filaments of poly-4-hydroxybutyrate. The filaments may comprise a dispersed tissue growth promoter 112 as shown somewhat schematically in FIG. 6A or a tissue growth promoter 114 may be applied to the porous cap 110 membrane as a coating or as an adsorbed layer, as shown in FIG. 6B, in a later step.

Figure 3:
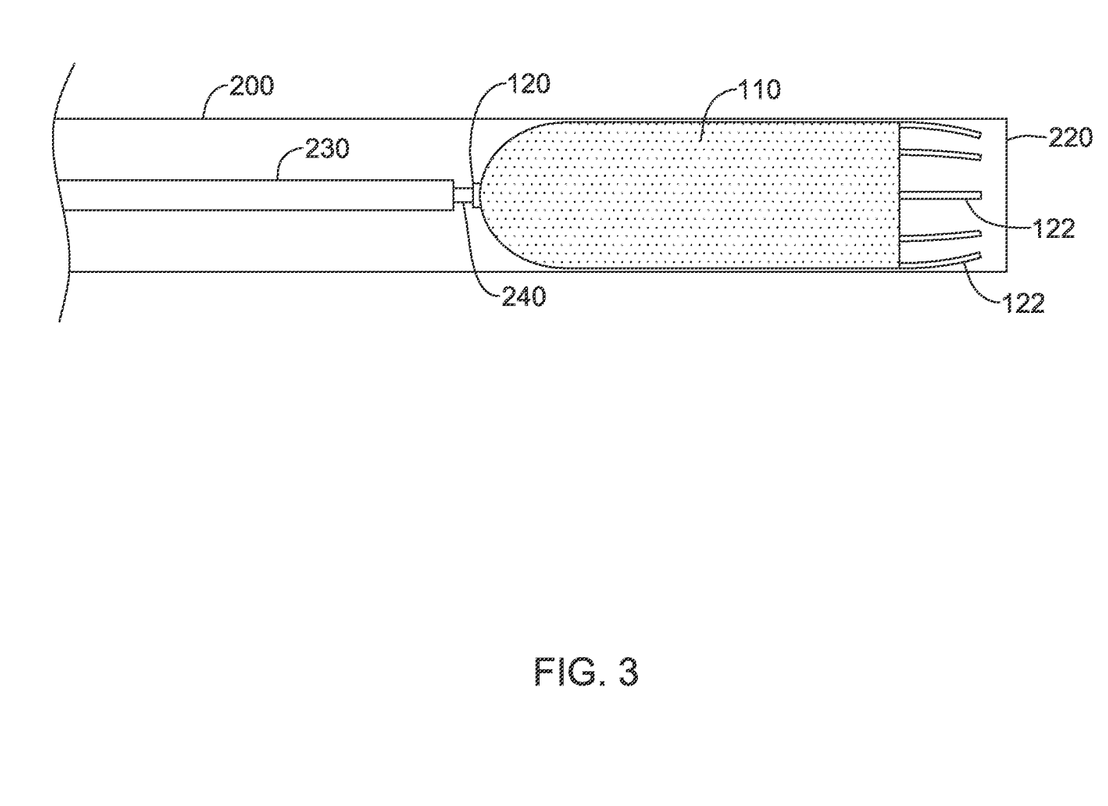
FIG. 3 presents a partial cutaway view of a left atrial appendage closure device of the invention disposed in a distal portion of a delivery catheter.

The bioabsorbable left atrial appendage closure devices 100 of FIGS. 1 and 2 may be delivered to the left atrial appendage using delivery catheters and approaches of the art. For example, the bioabsorbable left atrial appendage closure devices 100 of FIGS. 1 and 2 may be caused to assume a first compact configuration adapted to be received within the distal end of a delivery catheter 200, as shown in FIG. 3, prior to being advanced to the deployment site where the devices may be expelled by advancement of delivery shaft 230 and/or withdrawal of delivery catheter 200. In such aspects, the bioabsorbable left atrial appendage closure device 100 may include a proximal hub 120 adapted to releasably mate with a delivery shaft 230, one aspect of which is illustrated in FIG. 4.

Figure 4:
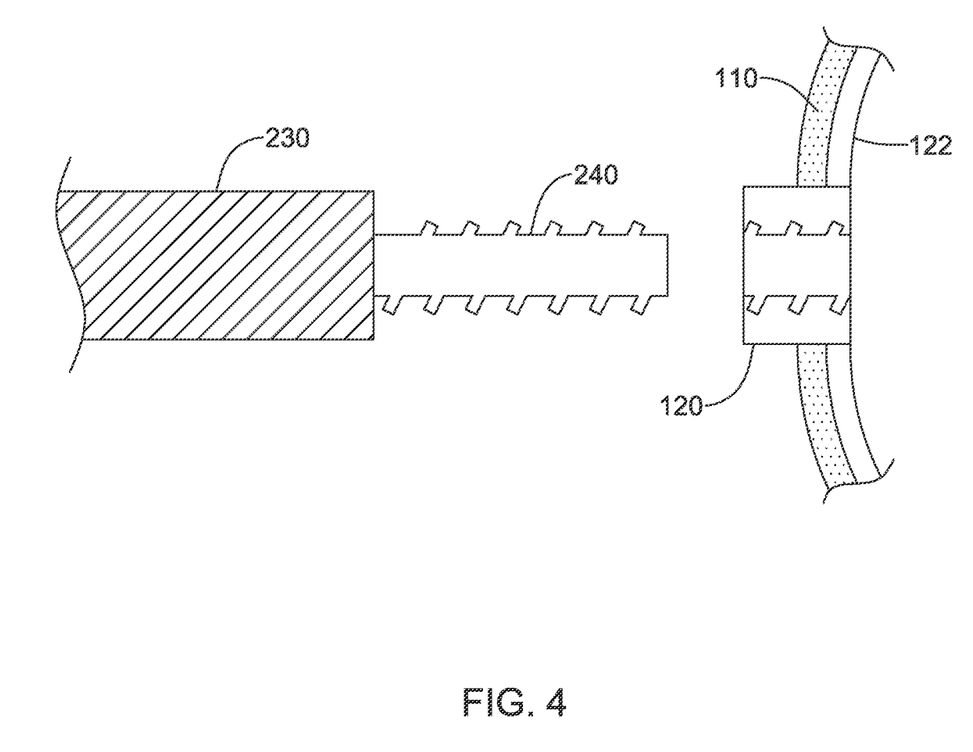
FIG. 4 presents a detail view of a releasable connection between a delivery shaft and a hub of a left atrial appendage closure device of the invention.

In the illustrated aspect of FIG. 4, the distal tip 240 of the delivery shaft 230 includes a male threaded portion and the corresponding mating hub 120 of the bioabsorbable left atrial appendage closure device 100 includes a female threaded aperture adapted to threadably engage the distal tip 240 for delivery through and from the delivery catheter 200, including possible recollapse and repositioning within the delivery site before rotation of the deliver shaft and distal tip 240 unscrews the distal tip 240 from the mating hub 120 of the bioabsorbable left atrial appendage closure device 100. It will be appreciated that engagement between the delivery site wall upon self-expansion of the bioabsorbable left atrial appendage closure device 100 to assume a second expanded configuration will provide the resistance necessary to allow the distal tip 240 to unscrew from the mating hub 120.

It also will be appreciated that other releasable mating connectors known in the art may be used. For example, the female threaded portion of the releasable mating connector may be formed within distal tip 240, while the hub 120 includes a mating male threaded portion. In the alternative, friction fit couplings, pin and loop connectors, and even magnetic couplers may be used with due regard for bioabsorbability of the components of the hub 120. The delivery catheter 200 and/or the delivery shaft 230 may include radiopaque markers to aid in positioning the left atrial appendage closure device 100 within the left atrial appendage.

Although the illustrative examples described above relate to closure of a left atrial appendage, it is also contemplated that the device may be used close other ostia such as that of an aneurysm. In such an aspect, the size and shape of the generally planar central region of the proximal portions of the bioabsorbable struts and porous cap as well as the distal extent of the device as a whole may be modified to better match the ostium and depth of the aneurysm or other lumen.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A left atrial appendage closure device comprising:
    a plurality of bioabsorbable struts having a proximal end and a distal end which are joined at their proximal portions to form an umbrella-like support structure which is concave when viewed from a distal end of the plurality of bioabsorbable struts,
    wherein the umbrella-like support structure has a first compact delivery configuration and a second expanded deployed configuration in which the umbrella-like support structure has a proximal circumferential dimension sized and adapted to span and engage an ostium of a left atrial appendage and a longitudinal extent sized and adapted to be contained within the left atrial appendage;
    a bioabsorbable porous cap coextensive with the joined proximal portions of the bioabsorbable struts and which extends distally therefrom along at least a portion of the umbrella-like support structure sized and adapted to be contained within the left atrial appendage,
    wherein the pores of the bioabsorbable porous cap are sized and adapted to retain thrombi within the left atrial appendage when the left atrial appendage closure device is deployed within the left atrial appendage, and the bioabsorbable porous cap includes a tissue growth promoting component,
wherein the plurality of bioabsorbable struts and the bioabsorbable porous cap are integrally formed from a single polymer.

2. The left atrial appendage closure device of claim 1, wherein the bioabsorbable porous cap is selected from the group consisting of a textile, a nonwoven, a braid, a laser cut sheet, an etched sheet, and a 3D printed article.

3. The left atrial appendage closure device of claim 1, wherein the single polymer is selected from the group consisting of polyglycolic acid, polylactic acid, polycaprolactone, polyvalerolactone, poly(1,4-dioxane-2,3-dione), poly(1,3-dioxane-2-one), poly(p-dioxanone), poly(1,5-dioxepan-2-one), poly(P-R,S-malic acid), poly($\alpha$-malic acid), polyhydroxyalkanoates, and mixtures or copolymers thereof.

4. The left atrial appendage closure device of claim 1, wherein the tissue growth promoting component is selected from the group consisting of fibronectin, vascular endothelial growth factor, and fibroblast growth factor.

5. The left atrial appendage closure device of claim 1, wherein tissue growth promoting component is a layer on the bioabsorbable porous cap.

6. The left atrial appendage closure device of claim 1, wherein tissue growth promoting component is dispersed within the bioabsorbable porous cap.

7. The left atrial appendage closure device of claim 1, wherein tissue growth promoting component is absorbed within a surface layer of the bioabsorbable porous cap.

8. The left atrial appendage closure device of claim 1, wherein thicknesses of the plurality of bioabsorbable struts and the bioabsorbable porous cap are selected to provide a controlled bioabsorption profile which minimizes release of particulate material.

9. The left atrial appendage closure device of claim 1, further comprising a hub attached to the plurality of bioabsorbable struts and adapted to be releaseably attached to a distal end of a delivery shaft.

* * * * *